United States Patent
Lyons et al.

(10) Patent No.: US 8,249,889 B2
(45) Date of Patent: Aug. 21, 2012

(54) PROVIDING INFORMATION REGARDING A PRODUCT

(75) Inventors: Nicholas P. Lyons, Sunnyvale, CA (US); Nina Trappe Bhatti, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2653 days.

(21) Appl. No.: 11/047,016

(22) Filed: Jan. 31, 2005

(65) Prior Publication Data

US 2006/0169773 A1    Aug. 3, 2006

(51) Int. Cl.
| | |
|---|---|
| G06Q 10/00 | (2012.01) |
| G06Q 50/00 | (2012.01) |
| A61B 5/00 | (2006.01) |
| G06F 19/00 | (2011.01) |

(52) U.S. Cl. .......... 705/2; 705/3; 705/7.11; 705/7.22
(58) Field of Classification Search .................. None
See application file for complete search history.

(56) References Cited

U.S. PATENT DOCUMENTS

| | | |
|---|---|---|
| 5,151,684 A | 9/1992 | Johnsen |
| 5,874,896 A | 2/1999 | Lowe et al. |
| 5,933,829 A | 8/1999 | Durst et al. |
| 5,978,773 A | 11/1999 | Hudetz et al. |
| 6,108,656 A | 8/2000 | Durst et al. |
| 6,129,274 A | 10/2000 | Suzuki |
| 6,169,483 B1 | 1/2001 | Ghaffari et al. |
| 6,169,975 B1 | 1/2001 | White et al. |
| 6,179,206 B1 | 1/2001 | Matsumori |
| 6,199,048 B1 | 3/2001 | Hudetz et al. |
| 6,199,753 B1 | 3/2001 | Tracy et al. |
| 6,294,999 B1 * | 9/2001 | Yarin et al. ............. 340/573.1 |
| 6,542,933 B1 | 4/2003 | Durst, Jr. et al. |
| 6,572,016 B2 | 6/2003 | Saveliev et al. |
| 6,594,549 B2 | 7/2003 | Siegel |
| 6,604,650 B2 | 8/2003 | Sagar |
| 6,614,351 B2 | 9/2003 | Mann et al. |
| 6,616,047 B2 | 9/2003 | Catan |
| 6,628,199 B1 | 9/2003 | Ehrensvard et al. |

(Continued)

OTHER PUBLICATIONS

Butschli, J., "VA Hospital Tests 'Talking' Label", Packworld.com, http:// www.packworld.com/cds_print.html?rec_id=12555, downloaded Jan. 31, 2005.

(Continued)

*Primary Examiner* — Robert Morgan
*Assistant Examiner* — Eliza Lam (57) ABSTRACT

Interactive information regarding a product in a package is provided. A unique identifier is received. The unique identifier identifies a package containing a product. Use information is generated based at least partially on stored user information regarding past use of the product.

20 Claims, 6 Drawing Sheets

U.S. PATENT DOCUMENTS

| | | |
|---|---|---|
| 6,702,146 B2 | 3/2004 | Varis |
| 6,732,884 B2 | 5/2004 | Topliffe et al. |
| 6,950,939 B2 | 9/2005 | Tobin |
| 6,985,870 B2 * | 1/2006 | Martucci et al. .................. 705/3 |
| 7,080,041 B2 | 7/2006 | Nagel |
| 7,127,261 B2 | 10/2006 | Van Erlach |
| 7,152,047 B1 | 12/2006 | Nagel |
| 2002/0117544 A1 | 8/2002 | Wolf et al. |
| 2003/0195818 A1 | 10/2003 | Howell et al. |
| 2003/0227392 A1 | 12/2003 | Ebert et al. |
| 2004/0010425 A1 * | 1/2004 | Wilkes et al. .................... 705/3 |
| 2004/0070491 A1 | 4/2004 | Huang et al. |
| 2004/0079804 A1 | 4/2004 | Harding et al. |
| 2004/0128555 A1 | 7/2004 | Saitoh et al. |
| 2005/0108659 A1 | 5/2005 | Philyaw |
| 2005/0114270 A1 | 5/2005 | Hind et al. |
| 2006/0187048 A1 | 8/2006 | Curkendall et al. |
| 2007/0276984 A1 | 11/2007 | Schuesslar |

OTHER PUBLICATIONS

Want, R., "The Magic of RFID", vol. 2, No. 7, Oct. 2004, Intel Research, http://www.acmqueue.com/modules.php?name=Content&pa=showpage&pid=216, downloaded Jan. 31, 2005.

Reynolds, P. et al., "Packing Delivers for Pharmaceutical and Medical Firms", Packworld.com, http://www.packworld.com/cds_print.html?rec_id=18114, downloaded Jan. 31, 2005.

Chappell G et al—"Audio-ID in the Box: The Value of Auto-ID Technology in Retail Stores"—Accenture—Feb. 2003.

* cited by examiner

PROVIDING INFORMATION REGARDING A PRODUCT

BACKGROUND

Products sold to customers sometimes have instructions that may be confusing. For example, for products that are consumed some instructions may include requirements such as a minimum amount that must be used or a maximum amount that may be used of a product. Other examples of instructions are instructions requiring that a product be used a certain number of times in a predetermined period of time or instructions specifying the types of other products that can or cannot safely be used with the product.

For a customer, keeping track of instructions and activity associated with the instructions may be confusing. For example, some customers may not be able to read the instructions. And, even if the customer is able to read the instructions, the customer may not be able to keep track of all of the activity that is associated with the instructions. For example, a customer may forget if he has already taken a dose of a medicine.

In the case of pharmaceuticals, keeping track of when to take prescribed medication may be a complex organizational task. Some people use boxes divided into days of the week and, sometimes, time of day to ensure that the proper medication is taken at the proper time. Thus, a person may fill up the divisions of a medication box once a week, and take the medication in each division of the box at the time of day indicated on the division.

This organizational technique, although technologically simple, is prone to manual error. For example, the person may be visually impaired, and misread the dosage listed on a package. In another example, if the person is cognitively impaired, the person may get confused about the day, and take medicine meant to be taken the following day, thus doubling the dose. Further, the boxes provide limited information to the user beyond day, and sometimes time, the medicine is to be taken. For example, the boxes don't mention whether the medicine is to be taken on an empty stomach or after a meal, etc.

SUMMARY

Providing interactive information regarding a product in a package is described. A unique identifier is received. The unique identifier identifies a package containing a product. Use information regarding use of the product is generated based at least partially on stored user information regarding past use of the product.

BRIEF DESCRIPTION OF THE DRAWINGS

Features of the present embodiments will become apparent to those skilled in the art from the following description with reference to the figures, in which.

DETAILED DESCRIPTION

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the embodiments may be practiced without limitation to these specific details. In other instances, well known methods and structures have not been described in detail so as not to unnecessarily obscure the embodiments. The embodiments herein will be described using an example of a pharmaceutical product, such as medicine that is prescribed to a user. It will be understood that the description of the embodiments may be extended to any type of product.

A method and system for providing information regarding use of a product is described. The information provided may include any form of information including audio, visual, touch sensitive information, and various types of alerts. For example, the information may be in the form of Braille, a magnified display, and audio instructions. A user or other authorized person may customize the form of information provided. For example, a user may specify whether to receive instructions through an audio device or a display. The user may also specify the number of alerts or reminders, who is alerted and the number of people that are alerted if the user fails to follow instructions. Many other customizations may be implemented as is known in the art.

The information providing system may be initiated by reading a unique identifier from an information source, such as a package, a card, a hospital bracelet, a hospital chart, or another source on which information regarding a medication or patient may be stored. The unique identifier may be stored in any type of medium. For example, the unique identifier may be stored directly on the information source as a serial number or a bar code, in a radio frequency identification ("RFID") tag, or in an embedded microprocessor. The information provided may include when the product is to be used next, when the product has been used previously, and/or if the product may be used at the time the unique identifier is read. Providing the information may also include providing alerts indicating when the product is to be used. The alerts may include escalating alerts, where each alert escalates in urgency when a previous alert does not receive a response from a user. The escalation may include alerts transmitted to a doctor or may be customized by the user. For example, the user may set the second alert to be transmitted to a relative. In some implementations, the last level of alert may be set so that it may not be changed. For example, the last level of alert may include transmitting an alert to an emergency response service such as by accessing the "911" service for the user's area.

The information providing system may also allow interaction at a server from a provider or prescriber of a product. For example, a doctor may change a dosage or timing of a medication that the doctor prescribed to a patient by finding the medication in a data store administered by the server, and directly change prescription information in the data store.

RFID tags are typically programmed with unique identification codes that identify the object. For example, the unique identification codes may include unique identifiers, which uniquely identify each package of a product. RFID tags use radio frequency technology to transmit information stored in the RFID tags. For example, a RFID tag may include an integrated circuit and an antenna. The RFID tag may include a passive RFID tag (not using an internal power source such as a battery) or an active RFID tag (using an internal power source, such as a battery) may be used.

Figure 1:
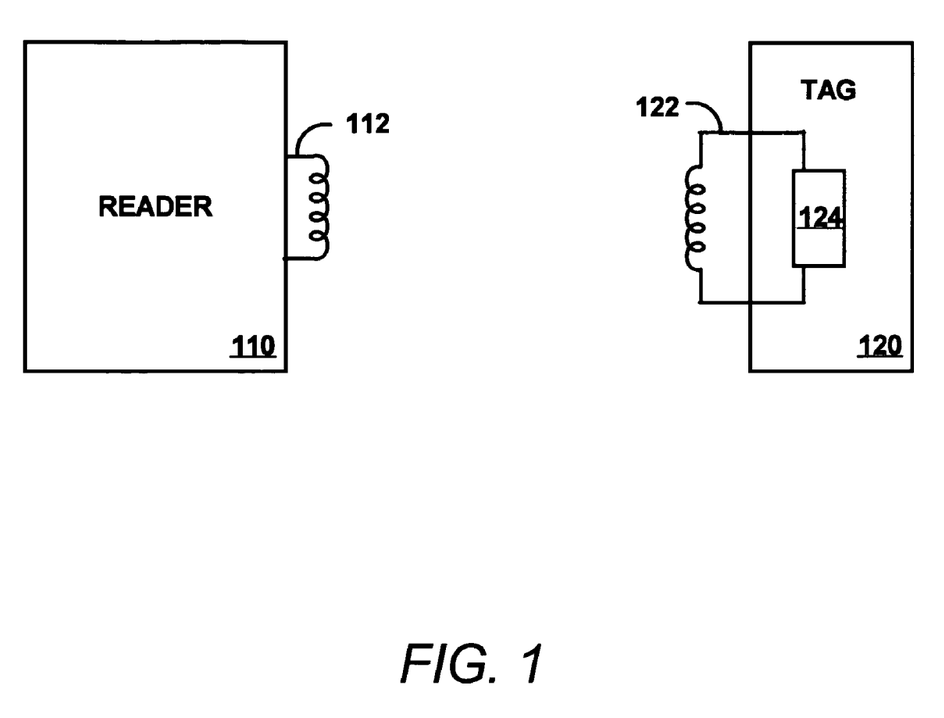
FIG. 1 illustrates a conventional RFID reader and tag.

As shown in FIG. 1, a reader 110 may read a RFID tag 120. The RFID tag 120 and reader 110 system may be used in the embodiments described. A reader 110 may include an inductive element 112 generating a magnetic field that energizes a tag 120. The inductive element 112 may be part of an antenna. The magnetic field induces an energizing signal for powering the tag 120 via the antenna. The RFID tag 120 may include an inductive element 122 and tag electronics 124. When the tag 120 is in proximity of the reader 110, the magnetic field generated by the reader 110 energizes the tag 120 by inducing a voltage across the inductive element 122 and providing power to the tag electronics 124. Information in the tag 120 is sent back to the reader 110 using the tag electronics 124 and the inductive element 122 by alternating the loading of the inductive element 122 in a pattern corresponding to the data being sent to the reader 110. This technique is known as load modulation.

FIG. 1 illustrates a passive RFID tag using load modulation. Other types of passive tag technology may be used. Also, instead of a passive tag, an active RFID tag with a power source, such as a battery, may be used. Also, instead of an RFID tag, any type of medium storing or representing a unique ID, which may be read with some type of reader, may be used. Examples of ID technologies suitable for this purpose include, but are not limited to, one and two dimensional barcodes (such as UPC), active and passive low, medium and high frequency RFID tags (such as EPC, ISO 14443 A+B, ISO 15693 RFID tag families).

Figure 2A:
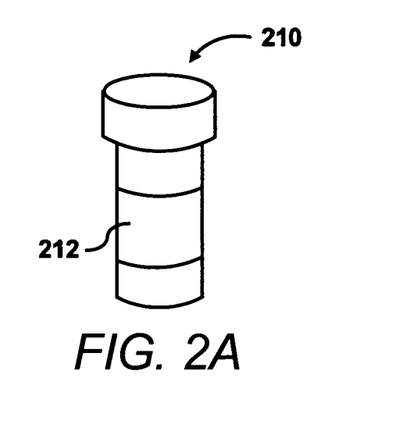
FIGS. 2A and 2B illustrate an example of a product including an RFID tag.
Figure 2B:
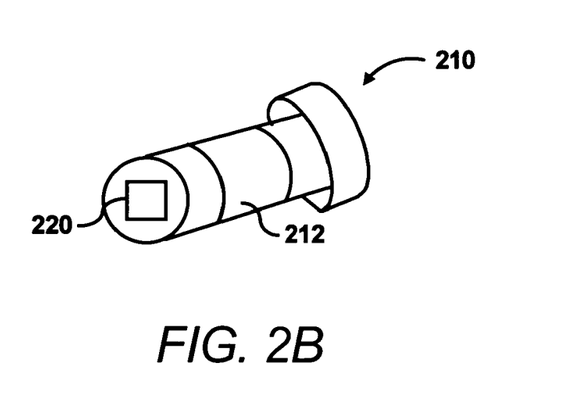

FIGS. 2A and 2B illustrate a package 210 including an information tag 220. The information tag 220 may include a bar code, print or a label on the package 210, an embedded microprocessor, a RFID tag or another medium. The information tag 220 may store a unique identifier. The unique identifier may include a package identifier for the package 210 or a user identifier, identifying the user using the product in package 210.

If the information tag 220 includes a RFID tag or embedded microprocessor, the unique identifier may be stored alone in the RFID tag or embedded microprocessor. In addition, if the RFID tag includes a sufficient amount of memory, the RFID tag may be configured to store additional information regarding a user of a medication or the user's use of the medication until the information may be transferred to a data store.

Although the package 210 is shown to be a pill bottle, such as a pharmaceutical pill bottle, any type of package may be used in accordance with the embodiments described. The package 210 may be of any shape, such as a cube, or any material, such as some type of paper or plastic. The package 210 may be configured to contain any type of product.

In the example shown, the package 210 includes a label 212. The label 212 may include instructions on use of the product in the package 210. The information tag 220, as shown, is placed at the bottom of the package 210 to allow the package to be moved within the reader's scan area in an upright position. However, this is for user convenience and not a requirement of the system. The information tag 220 may be placed on any part of the package 210 depending on design.

In other embodiments, the information tag 220 may be placed on or stored in a card assigned to the user, a bracelet worn by the user or on a hospital chart in association with the user's name.

The user interaction model is more complicated in a hospital or other institutional setting in order to track responsibility for correct use of medications in what can at time be a confusing and hectic environment. This interaction is described in examples below in greater detail.

Figure 3:
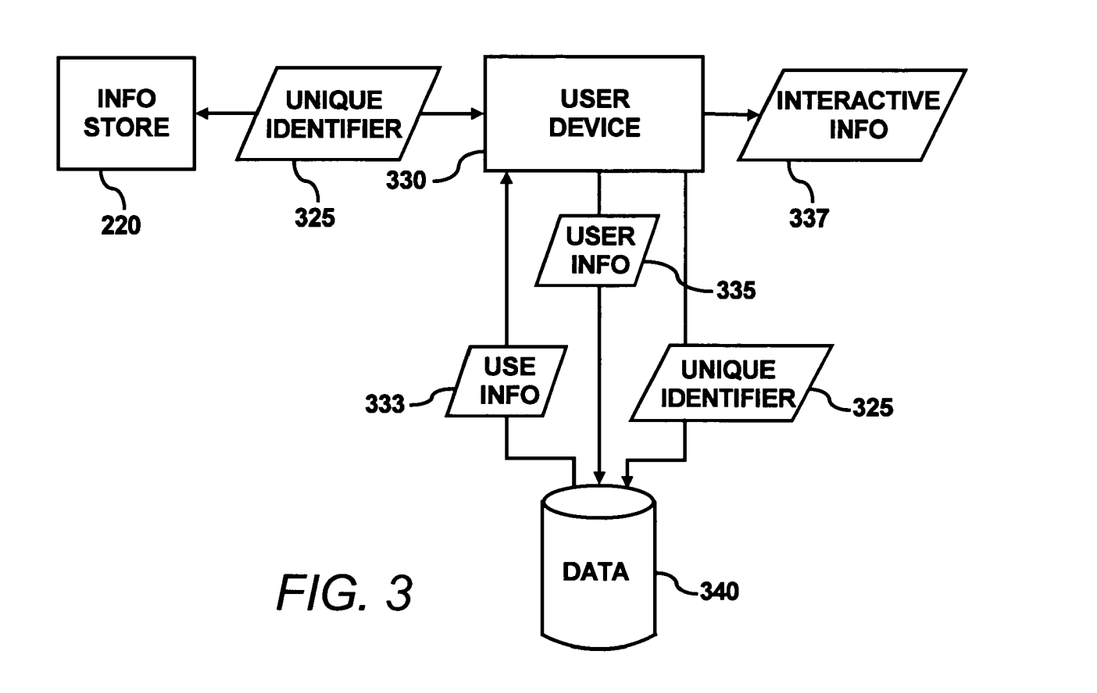
FIG. 3 illustrates an example of an interactive audio product information system.

FIG. 3 illustrates the movement of data through an information providing system 300. Information may be read from the information tag 220 by a user device 330. The information tag 220 may include a unique identifier 325. As described above, the unique identifier may include a package identifier or a user identifier. The user device 330 may also read other information that is stored in the information tag 220. For example, the information tag 220 may store information regarding when a user last took medication.

In one example, the information tag 220 may include an intermittent type RFID tag. An intermittent RFID tag may include a switch between the integrated circuit and antenna in the RFID tag. The intermittent RFID tag may include the RFID tag configured to receive user input described in U.S. patent application No. 10/950,102, filed Sep. 24, 2004.

A user may press the RFID tag to enter information into the RFID tag, which is stored until the RFID tag is read by the user device 330. The purpose of pressing the intermittent RFID tag allows the user to demonstrate intent to complete a related action or declare a significant change of state. For example, the RFID tag may include various sections having labels such as "yes," "no," "up," or "down." The user may press any of these sections, depending on the action the user wants to take or the information the user wants to impart. The user may be presented with the question "Do you want to take your medication now?" If the user will take the medication at that time, the user may depress the "yes" section of the RFID tag. In another example, if the user is looking at a display, and wishes to scroll through the display, the user may depress either the "up" or "down" sections of the RFID tags.

In another example, information specific to the product and/or user of the product in the package 210 for use in providing information may be stored in the information tag 220. For example, if the package 210 is a large stock supply of a medication in a hospital, the information tag 220 may store a list of unique identifiers identifying users using the medication or store a list of users using the medication. If the information tag 220 is on a card or a bracelet associated with a user, the information tag may include a pointer or database key to a list of unique identifiers identifying medication used by the user or a list of medication used by the user.

The user device 330 uses the unique identifier 325 to search a data store 340. The data store 340 may include any type of storage medium in one or more devices. Also, data store 340 may include a database or some other type of storage mode. Although the data store 340 is shown to be outside of the user device 330, in some embodiments, the data store 340 may at least partially lie within the user device 330.

The data store 340 transmits use information 333 for the product or user identified by the unique identifier 325 to the user device 330. The use information 333 may include information regarding use of the product in the package 210 based on past use of the product in the package 210. In the example of a pharmaceutical product, the use information 333 may include information regarding the medicine, such as information on the label 212, if another dose of a medicine is to be taken at the time the information tag 220 is read by the user device, when the next dose of the medicine is to be taken, when a previous dose of the medicine was taken or auxiliary information regarding the medicine's usage, such as a message from the user's doctor asking the user to call the doctor's office.

The user device 330 outputs the use information 333 as interactive information 337 in a form selected by the user. The interactive information 337 may include any form of information. The interactive information 337 may include audio information, Braille, video information, text information, alerts, or any other form specified by the user or an authorized person. For example, the interactive information 337 may include displaying a text message on the user's television screen indicating that it is time for the user to take a dose of the user's medication.

Figure 4:
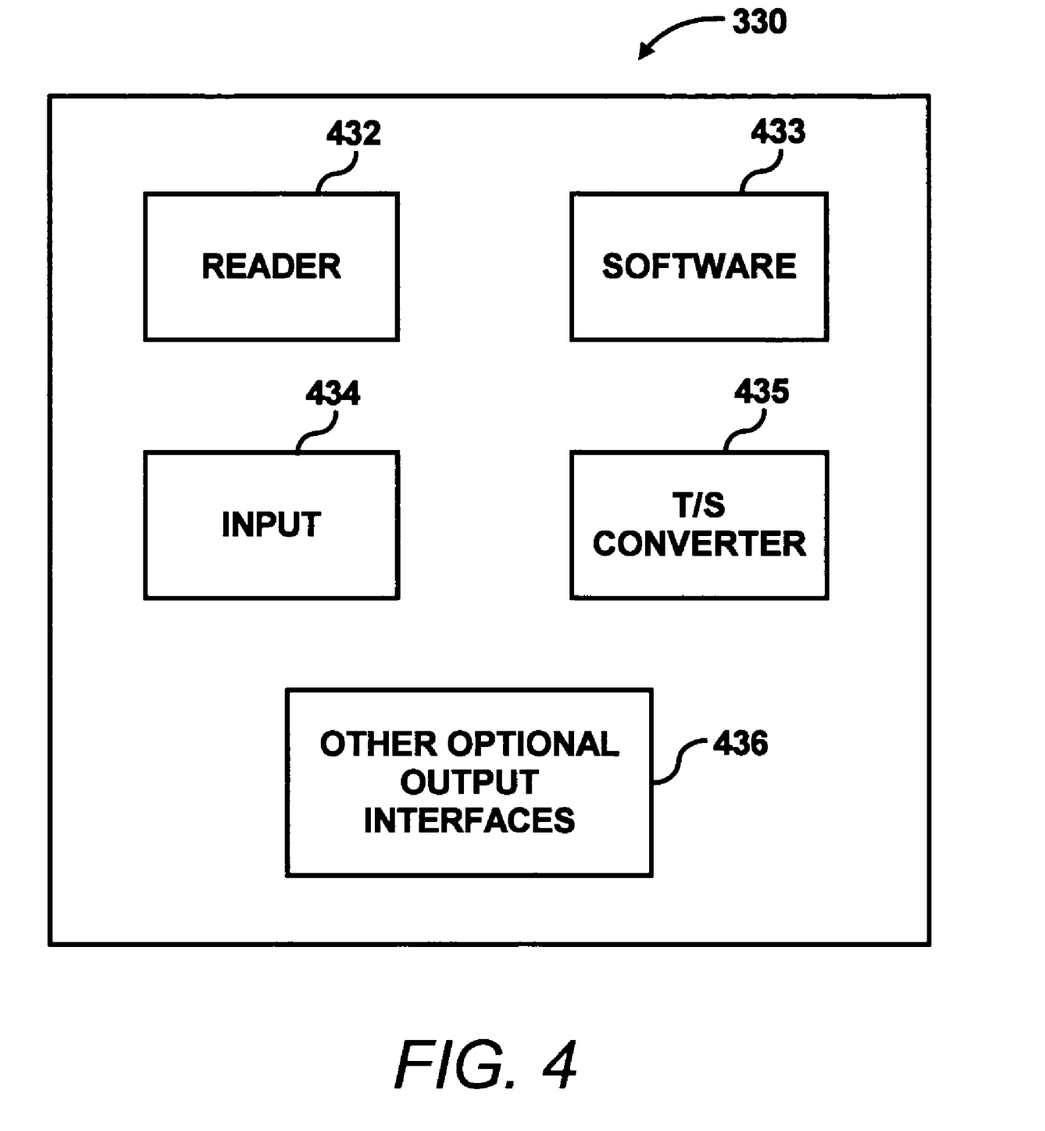
FIG. 4 illustrates an example of a user device usable to provide interactive product information.

The use information 333 may be stored in a data store 340 in any format. The user device 330 may generate the use information 333 as interactive information 337 using a software program. For example, if the interactive information 337 is audio information or video information, the user device 330 may generate the interactive information 337 using software capable of outputting audio or video information. In another example, if the use information 333 is stored as a text file and the interactive information 337 is to be generated as audio information, the user device 330 may convert the text information to audio information using a text to speech converter (as shown in FIG. 4). In other examples, the interactive information 337 may be generated by a server, as discussed below with reference to FIG. 5.

The user device 330 may also receive input of user provided information 335. The user device 330 transmits the received user provided information 335 to the data store 340. The user device 330 may include an input mechanism allowing the user to indicate that a use of the product in the package 210 has been made or is about to be made. For example, the user may press a button on the user device 330 indicating that the user is about to take a dose of the medicine in the package 210. In another example, the user may depress an intermittent RFID tag to indicate that the user is about to take a dose of the medicine in the package 210. The user device 330 reads this user provided information from the RFID tag. The user device 330 forwards the user provided information 335, whether entered by the user through the user device 330 or the RFID tag, to the data store 340 for use in providing future audio information to the user.

FIG. 4 illustrates a block diagram of an example of the user device 330. The user device 330 may include a dedicated device, used only to provide interactive information regarding products. The user device 330 may be part of another device, such as a mobile phone, a personal data assistant ("PDA"), a reading device or other type of computing or communications device. If the user device 330 is a part of another device, the hardware and software of the other device may be used to provide or may be augmented to provide the features described herein.

The user device 330 includes a reader 432 to read information from the information tag 220, as shown in FIGS. 2A, 2B and 3. The user device 330 may also include an input mechanism 434 and a text to speech ("T/S") converter 435. The input mechanism 434 may include any type of input mechanism, such as a keyboard, a mouse or one or more dedicated keys. For example, if the user device 330 is a dedicated device for pharmaceutical products, the input mechanism 434 may include one or more dedicated keys, such as a key indicating that a dose of the medication is about to be taken. The T/S converter 435 may be used to convert information stored as text to speech to allow the interactive information to be generated as speech. The T/S converter 435 may include any known type of T/S converter.

Another optional output interfaces module 436 may include software and/or hardware to support various types of output. For example, the other optional output interfaces module may support video, Braille or other output modalities.

The user device 330 may also include software 433. The software 433 may include software to generate the interactive information 337, as shown in FIG. 3. The software 433 may further include software 433 to exchange and process information, such as information from the information tag 220, information from the data store 340, or information received through a user input mechanism 434. For example, the user device 330 may receive past use information from the data store 340, and the user device 330 may include software 433 to determine if another dose of a medication needs to be taken by the user. However, the software to determine use information regarding the product may be located in a location remote to the user device 330, as shown in FIG. 5.

Figure 5:
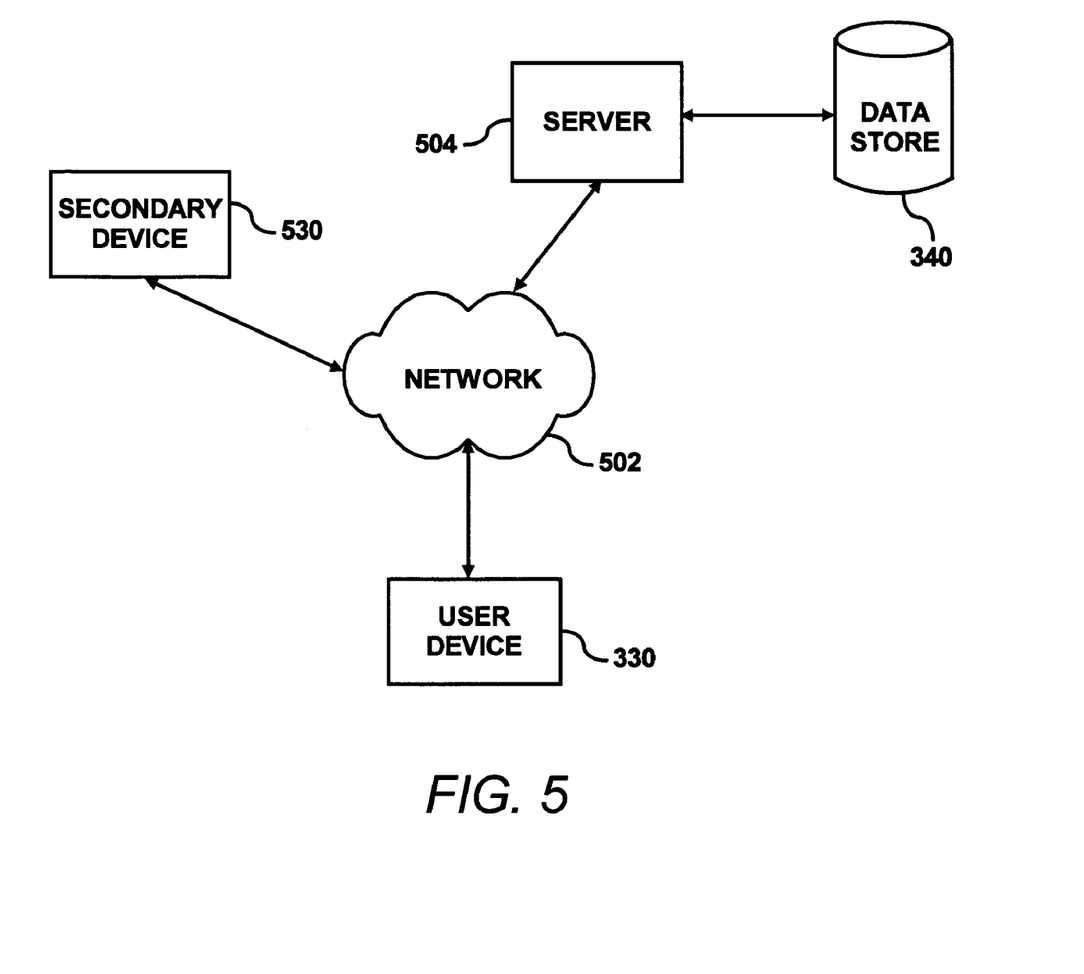
FIG. 5 illustrates an example of a product information system in communication with a server.

As shown in FIG. 5, the product information system can be implemented in a computing system that includes a back-end component, such as a server 504. The user device 330 may include a client computing device having a graphical user interface and/or a browser through which a user can interact with the server 504. The server 504 may include, be in communication with, or administer the data store 340. Thus, the data store 340 may communicate with the user device 330 through the server 504. As discussed above, the data store 340 may be included at least partially within the user device 330 or be directly connected to the user device 330 instead of communicating with the user device 330 through the server 504. For example, the data store 340 may be part of a local computer system. A part of the data store 340 may also include portions of the information tag 220, if the information tag 220 is configured to hold larger amounts of memory.

The information stored in the data store 340 may include a user profile for the user associated with the unique identifier 325 and prescription information, such as dose level, number of times the medicine should be taken, and the doctor prescribing the medicine. The information stored in data store 340 may further include the form of interactive information 337 that the user is to receive. In one example, the data store 340 may include patient information, such as a chart, for a user who is a patient in a hospital. In this example, the patient's chart may be updated as soon as the patient takes or is given medication.

The data store 340 may also include other information, such as auxiliary information stored by the user's doctor, including instructions for the user to call or see the doctor or results of medical tests. In one example, the auxiliary information may be provided to the user when the user device 330 is in communication with the server 504. In another example, an alert may be generated to indicate to the user that there is auxiliary information awaiting the user, and that the user should connect the user device 330 to the server 504.

In operation, the user device 330 may transmit information, such as the unique identifier 325 and user provided information 335, to the server 504. The server 504 may transmit information such as use information, including past and future use information to the user device 330.

The server 504 may transmit information such as a user profile or, in the case of pharmaceuticals, dose and interval information, to the user device 330 for the user device 330 to process. The user device 330 may process the information received from the server 504 to determine use information to present to the user in a selected interactive information form.

Alternatively, the server 504 may include software to process information from the data store 340 to determine use information for the user. The server 504 may transmit the use information to the user device 330, which the user device transmits to the user in a selected interactive form.

A secondary device 530 may also communicate with the server 504. For example, the secondary device 530 may be used by doctors or other authorized persons to update prescriptions or leave messages for patients. The secondary device 530 may also be used by other individuals authorized by users to access the users' usage information. Thus, family members or medical professionals may be able to monitor the user's medicine usage remotely. The secondary device 530 may include a mobile telephone, a PDA or any type of computing device.

The components of the system can be interconnected by any form or medium of digital data communication, e.g., a network 502. The network 502 may include a wired network or a wireless network.

Figure 6:
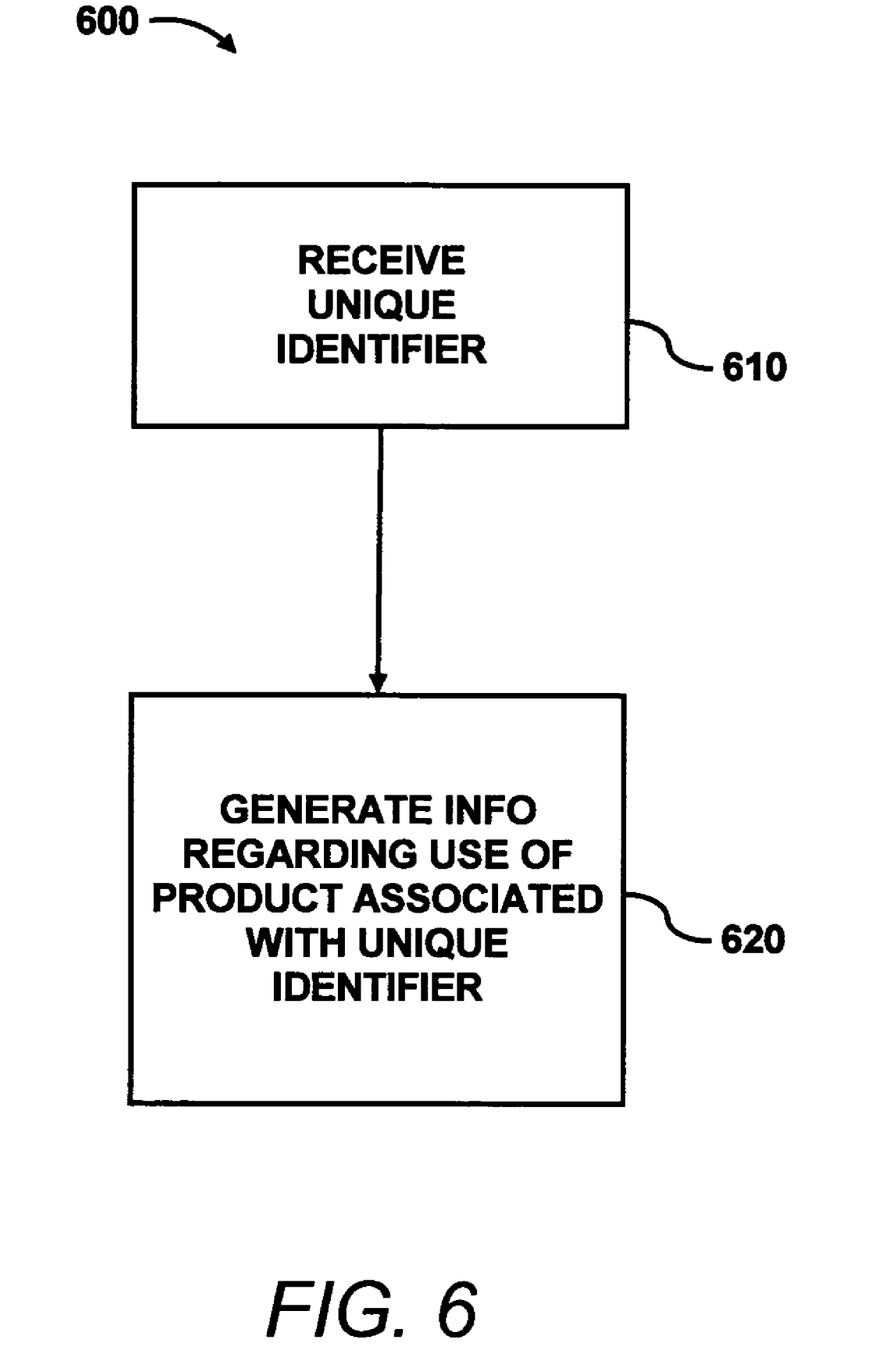
FIG. 6 illustrates an example of a method of providing interactive information.

FIG. 6 illustrates a method of providing interactive audio information regarding a product in a package. At step 610, the user device 330 receives the unique identifier 325, as shown in FIGS. 3-5. As shown in FIG. 3, the unique identifier 325 may be read from a RFID tag 220 by a user device 330. The unique identifier 325 may be read using the user device 330 by the user, such as the person receiving the medication or another authorized person, such as a nurse or doctor.

The user device 330 may also be configured to read one or more second unique identifiers (not shown). The second unique identifier may identify a user as performing a specific role in relation to the tagged item, such as the person receiving the medication or an authorized person dispensing the medication, such as a nurse. For example, if the unique identifier 325 is read by an authorized person where there are many patients present, the authorized person may read a second unique identifier, identifying the user, to ensure that the authorized person is giving the medication to the right patient. The authorized person may also use the user device 330 to read another second unique identifier identifying the authorized person.

The second unique identifier identifying the authorized person may be stored in data store 340 along with a particular instance of a patient receiving medication to identify the person who dispensed the medication to the patient at the particular instance. For example, people fulfilling certain roles in the dispensing of the medicine, in addition to individual doses of medicine, may be identified with an ID tag. A pharmacist, doctor, nurse and patient would be typical roles that may have ID tags. A user may scan his/her 'role ID tag' prior to scanning the medicine's tag, and the information delivered may be customized to fit the user's role. A doctor in this scenario may be presented with information concerning more therapy treatment options, for example. A patient would have his ID tag scanned, and his medicine dosage scanned, to act as a check that the proper medication and amount is being administered.

A nurse scanning her own tag followed by scanning the ID tag of a medicine would inform the nurse that this particular dose of a medicine is intended for a specified patient at a specified time. The ID tag of the medicine may also provide the nurse with the capability of tracing the medicine back to the prescribing doctor.

The second unique identifier may be placed on a bracelet, such as a hospital ID bracelet, a personal identity card or other identification medium that may be associated with the user.

The unique identifier 325 may be used to retrieve information from the data store 340. The unique identifier 325 may be used to search for information specific to the package 210, shown in FIG. 2, associated with the unique identifier 325. The user device 330 may transmit the unique identifier 325 over a network 502 to a server 504 to search the data store 340, if the data store 340 is connected to the user device 330 through the network 502.

In the example where an authorized user, such as a nurse reads the unique identifier, the data store 340 may store a user identifier, identifying the user of the medication. Thus, if a nurse in a hospital wishes to give medication to a patient (user), the nurse may use a user device 330 to read the unique identifier 325 from the package. The nurse may also use the user device 330 to read the second unique identifier from the patient's hospital ID bracelet. If the second unique identifier does not match the user identifier stored in association with the unique identifier, an alarm or other indication may be provided to the nurse that the wrong patient is about to receive medication. In one embodiment, the alarm may include a series of escalating alarms. Each time an alarm is not acknowledged, the next alarm in the series of escalating alarms is generated. If the second identifier does match a stored patient identifier, either an indication that the patient is the correct patient to receive the medication will be provided to the nurse or no indication regarding whether the patient is the correct patient will be provided.

In another example, a single package may be used by several users. For example, a non-prescription medicine, such as vitamins, may be prescribed for various members of a family or a stock bottle in a hospital may be used to provide medication to several patients. If the medication in the bottle is not redistributed to each patient's own bottle, the unique identifier 325 for a particular user of the medication in the bottle may be stored in a card, a bracelet, a clipboard, or some other identification medium. The clipboard may include a list of users of the medication or an information medium including information regarding the particular user, such as a list of medications for the user.

The user may scan the unique identifier 325 from the identification medium. For example, a nurse providing medication to a patient in a hospital may scan the unique identifier 325 from a clipboard. When the nurse indicates that medication has been provided to the patient associated with the unique identifier 325, the information that the patient has received the medication will be recorded immediately in an electronic record storing the patient's hospital chart. The patient's hospital chart may be stored, for example, in the data store 340.

At step 620, the user device 330 generates at least use information associated with the unique identifier 325. The use information may include, for example, information regarding the use of the product in the package. The use information may be based at least partially on stored user information regarding past use of the product ("past use information"). For example, if the use information includes information indicating that the user is to take another dose of a medication at the time the unique identifier is received, the past use information may include, for example, information indicating that the user has not taken a dose of the medication yet or that a prescribed time interval has passed since the user last took a dose of the medication. In addition to use information, other information may be generated by the user device 330, such as but not limited to alert information described in detail below and user identification information identifying the user for which the use information is intended.

As described above, the use information which is generated by the user device 330 in may be determined by software in either the user device 330 or the server 504. The use information may be determined based on one or more of the user profile, prescription information, and past use of the product by the user.

The method 600 may also include providing alerts to let the user know when a particular medication is to be taken. Once the unique identifier 325 has been received by the user device 330 or the server 504, the user device 330 or the server 504 may set up an alerting system based on the prescription information and user profile, taking into account past use of the medicine. The alerting system may be set up automatically through software in the user device 330 or software at the server 504.

For example, the server 504 may generate or transmit an alert to the user when the user is to take a dose of a medicine. The first alert may include a message to the user device 330 or a secondary device 530 which the user has assigned to receive alerts. If the first alert does not result in a response from the user, such as an indication through the user device 330 that the user has taken the dose, the server 504 may generate or transmit a second alert. The second alert may include an automated telephone call to the user. The alerts may keep escalating each time an alert does not receive a response. The third alert may include a call to a medical professional, such as a nurse or doctor, alerting the medical professional that the user is not responding. The fourth alert may include calling an emergency service, for example, calling "911." The alerts may be customized to what is desired by the user or an authorized person. For example, the user may want the second alert to be sent to the user's daughter-in-law. In another example, the user's doctor may want the second alert to be sent to a nurse.

The method 600 may also include receiving information from the product provider (such as a pharmaceutical company or pharmacist) or a product prescriber (such as a doctor, nurse or other authorized medical professional) using a secondary device 530 in the server 504. For example, the user's doctor may change prescription information stored in data store 340 so that the dosage level of the medicine and/or time interval for taking the medicine may be changed without the doctor being in possession of the package 210 or seeing the user. The doctor may also store messages for the user in data store 340. The messages received from the doctor may be transmitted from the server 504 to the user device 330 when the user causes the RFID tag 220 to be read by the user device. The message from the doctor may also be transmitted at any time, where the user device or another device alerts the user that a message has been received. For example, the user may assign a secondary device, such as a mobile phone, to receive alerts from the server if the mobile phone is not the user device 330. The user may then listen to the message through the user device 330 or accessing the server through the secondary device 530.

The method 600 may also include allowing an authorized individual to monitor the user's medicine intake through the server 504. For example, the authorized individual may access the server 504 through the secondary device 530. The authorized individual may login to the server using a password or other type of security measure. The authorized individual may access the user's records either using the unique identifier or user's name or some other type of identification.

Figure 7:
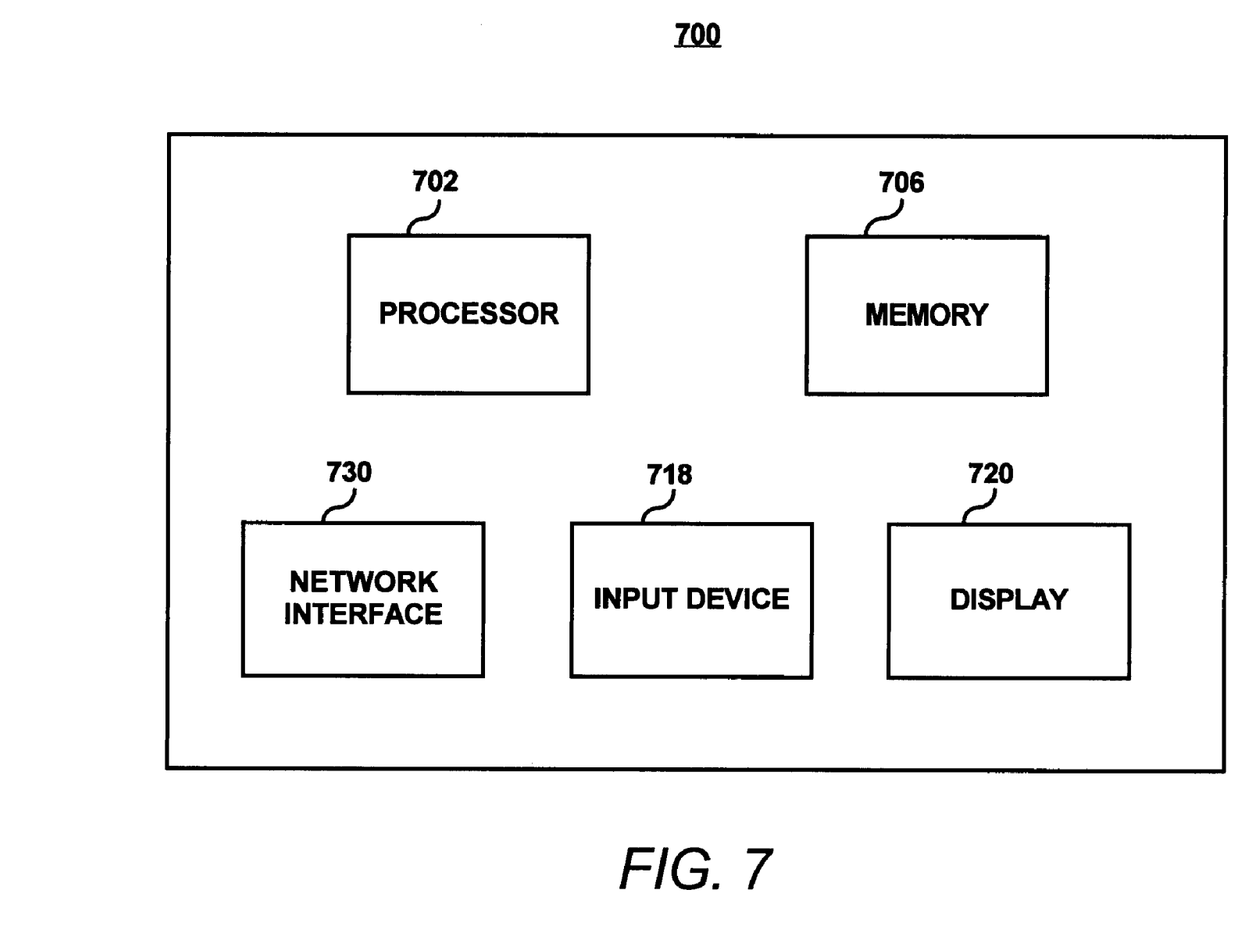
FIG. 7 is a block diagram illustrating a computer system operable to perform the method depicted in FIG. 6.

Referring to FIG. 7, and also with reference to FIG. 5, a schematic diagram of a computer system 700 is shown in accordance with an embodiment. The computer system 700 shown may be used as a server in the system shown in FIG. 5. The computer system 700 may include one or more processors, such as processor 702, providing an execution platform for executing software. The computer system 700 also includes a memory 706, which may include Random Access Memory (RAM) where software is resident during runtime. Other types of memory such as ROM (read only memory), EPROM (erasable, programmable ROM), EEPROM (electrically erasable, programmable ROM) and data storage, such as hard disks, etc., may be used.

A user interfaces with the computer system 700 with one or more input devices 718, such as a keyboard, a mouse, a stylus, and the like and a display 720. A network interface 730 is provided for communicating with other computer systems. It will be apparent to one of ordinary skill in the art that FIG. 7 is meant to illustrate a generic computer system. Any type of computer system may be used. Furthermore, one or more components of the components of the computer system 700 are optional, such as the display and input devices, and other types of components may be used or substituted as is known in the art.

One or more of the steps of the operation 600, as shown in FIG. 6, may be implemented as software embedded on a computer readable medium, such as the memory 706, and executed by the processor 702. The steps may be embodied by a computer program, which may exist in a variety of forms both active and inactive. For example, there may exist as software program(s) comprised of program instructions in source code, object code, executable code or other formats for performing some of the steps. Any of the above may be embodied on a computer readable medium, which include storage devices and signals, in compressed or uncompressed form. Examples of suitable computer readable storage devices include conventional computer system RAM (random access memory), ROM (read only memory), EPROM (erasable, programmable ROM), EEPROM (electrically erasable, programmable ROM), and magnetic or optical disks or tapes. Examples of computer readable signals, whether modulated using a carrier or not, are signals that a computer system hosting or running the computer program may be configured to access, including signals downloaded through the Internet or other networks. Concrete examples of the foregoing include distribution of the programs on a CD ROM or via Internet download. In a sense, the Internet itself, as an abstract entity, is a computer readable medium. The same is true of computer networks in general. It is therefore to be understood that those functions enumerated herein may be performed by any electronic device capable of executing the above-described functions.

What has been described and illustrated herein is an embodiment along with some of its variations. The terms, descriptions and figures used herein are set forth by way of illustration only and are not meant as limitations. Those skilled in the art will recognize that many variations are possible within the spirit and scope of the subject matter, which is intended to be defined by the following claims—and their equivalents—in which all terms are meant in their broadest reasonable sense unless otherwise indicated.

What is claimed is:

1. A method of providing information regarding a product, the method comprising:
   a reader that is a device receiving a unique identifier identifying a package containing a product;
   transmitting the unique identifier to the data store over a network;
   searching a data store storing at least part of use information for a user using the unique identifier; and
   generating at least the use information based at least partially on stored user information regarding past use of the product.

2. The method of claim 1, wherein receiving the unique identifier comprises reading the unique identifier from the package.

3. The method of claim 1, wherein receiving the unique identifier comprises receiving information stored in a radio frequency identification tag.

4. The method of claim 1, wherein generating the at least use information comprises:
   receiving at least part of the at least use information in a first form; and
   converting the at least part of the at least use information from the first form to a second form.

5. The method of claim 1, further comprising:
   receiving the at least use information from the data store.

6. The method of claim 1, wherein the product comprises a pharmaceutical product, and the at least use information comprises at least one of when a next dose of the product is to be taken, when a previous dose of a product was taken, and if a dose of the product is to be taken.

7. The method of claim 1, further comprising: receiving user information regarding use of the product from a user.

8. The method of claim 7, wherein receiving the user information regarding use of the product comprises receiving an input through a user device.

9. The method of claim 7, wherein receiving the user information regarding use of the product comprises receiving the user information regarding use of the product stored in a radio frequency identification tag.

10. The method of claim 1, further comprising receiving information from a secondary device.

11. The method of clam 1, further comprising providing past use information associated with the unique identifier to an authorized individual.

12. The method of claim 1, further comprising receiving a user profile, wherein generating the at least use information comprises generating the at least use information based at least partially on the user profile.

13. The method of claim 1, further comprising generating an alert, wherein the alert is an escalating alert and wherein the form of the alert escalates with each time no response to the alert is received.

14. The method of claim 1, further comprising gernerating an alert, wherein the alert is customized by at least one of a user and an authorized individual.

15. The method of claim 1, wherein the unique identifier comprises a first unique identifier, the method further comprising:
   reading a second unique identifier identifying the user.

16. The method of claim 15, further comprising:
   comparing at least one of a first information type associated with the second unique identifier and the second unique identifier to at least one of the first information type associated with the first unique identifier or a user identifier associated with the first unique identifier; and
   generating a wrong user alert if the at least one of the first information type associated with the second unique identifier and the second unique identifier does not match the at least one of the first information type associated with the first unique identifier or the user identifier associated with the first unique identifier.

17. The method of claim 16, further comprising generating one or more escalating wrong user alerts when a previous wrong user alert is not acknowledged.

18. The method of claim 15, wherein the user comprises a first user and the second unique identifier identifies a second user providing the product to the first user, the method further comprising:
   storing the second unique identifier in a data store in association with information regarding a particular instance of providing the product to the first user.

19. The method of claim 18, wherein generating the at least use information comprises generating the at least use information customized to a role of the user.

20. The method of claim 1, wherein generating the at least use information comprises generating the at least use information of a type customized for the user.

\* \* \* \* \*

UNITED STATES PATENT AND TRADEMARK OFFICE
CERTIFICATE OF CORRECTION

PATENT NO. : 8,249,889 B2  
APPLICATION NO. : 11/047016  
DATED : August 21, 2012  
INVENTOR(S) : Nicholas P. Lyons et al.

Page 1 of 1

It is certified that error appears in the above-identified patent and that said Letters Patent is hereby corrected as shown below:

In column 11, line 28, in Claim 11, delete "clam" and insert -- claim --, therefor.

Signed and Sealed this  
Fifth Day of February, 2013

Teresa Stanek Rea  
*Acting Director of the United States Patent and Trademark Office*